US012602239B2

(12) United States Patent
Voll et al.

(10) Patent No.: US 12,602,239 B2
(45) Date of Patent: Apr. 14, 2026

(54) SYSTEMS AND METHODS FOR RESOLVING AN ERROR CONDITION OF A MEDICAL DEVICE

(71) Applicant: Hill-Rom Services, Inc., Batesville, IN (US)

(72) Inventors: James D. Voll, Columbus, IN (US); Robert Mark Zerhusen, Batesville, IN (US); Nishita Vanita Shashikant, Batesville, IN (US)

(73) Assignee: Hill-Rom Services, Inc., Batesville, IN (US)

(*) Notice: Subject to any disclaimer, the term of this patent is extended or adjusted under 35 U.S.C. 154(b) by 173 days.

(21) Appl. No.: 18/495,015

(22) Filed: Oct. 26, 2023

(65) Prior Publication Data

US 2024/0145081 A1 May 2, 2024

Related U.S. Application Data

(60) Provisional application No. 63/381,669, filed on Oct. 31, 2022.

(51) Int. Cl.
*G06F 9/451* (2018.01)
*A61G 7/00* (2006.01)
(Continued)

(52) U.S. Cl.
CPC .............. *G06F 9/453* (2018.02); *A61G 7/00* (2013.01); *G06F 3/0482* (2013.01); *G06F 11/327* (2013.01); *G06F 16/955* (2019.01); *G06F 16/9554* (2019.01); *G16H 40/60* (2018.01); *G16H 40/67* (2018.01); *G06K 19/06028* (2013.01); *G06K 19/06037* (2013.01)

(58) Field of Classification Search
CPC .... G06F 9/453; G06F 3/0482; G06F 3/04847; G06F 11/327; G06F 16/9554; G06F 16/955; G16H 40/67; G16H 40/40; G16H 40/60; G16H 40/63; G06K 19/06028; G06K 19/06037; H04M 1/72415; A61G 7/00
See application file for complete search history.

(56) References Cited

U.S. PATENT DOCUMENTS 7,434,724 B2 10/2008 Lane
8,556,164 B1 10/2013 Freedman et al.
(Continued)

FOREIGN PATENT DOCUMENTS

EP 3790021 A1 3/2021

OTHER PUBLICATIONS

QR Planet: How can I preview the URL behind the QR Code? Oct. 4, 2022 [online], [retrieved on Jan. 23, 2024]. Retrieved from the Internet <URL:https://qrplanet.com/help/article/how-can-i-see-the-url-behind-the-qr-code>, pp. 1 to 8, especially pp. 2 to 3.

*Primary Examiner* — Nicholas Ulrich
(74) *Attorney, Agent, or Firm* — Barnes & Thornburg LLP

(57) ABSTRACT

A system and method for resolving an error condition of a medical device includes the medical device, a mobile device, and a host computer. The medical device generates a machine readable code, the machine readable code is read by the mobile device, and the remote computer hosts a uniform resource locator (URL) associated with the machine readable code such that the mobile device can access the URL.

20 Claims, 7 Drawing Sheets

(51) Int. Cl.

| | |
|---|---|
| *G06F 3/0482* | (2013.01) |
| *G06F 11/32* | (2006.01) |
| *G06F 16/955* | (2019.01) |
| *G06K 19/06* | (2006.01) |
| *G16H 40/60* | (2018.01) |
| *G16H 40/67* | (2018.01) |

(56) References Cited

U.S. PATENT DOCUMENTS

| | | | |
|---|---|---|---|
| 9,092,705 B2 | 7/2015 | Zhuang | |
| 9,530,087 B2 | 12/2016 | Borges et al. | |
| 10,026,505 B2 | 7/2018 | Lack et al. | |
| 10,185,834 B2 | 1/2019 | Adam et al. | |
| 11,197,105 B2 | 12/2021 | Perscheid | |
| 2012/0131416 A1* | 5/2012 | Dugan | G06F 11/32 |
| | | | 714/760 |
| 2012/0212455 A1 | 8/2012 | Kloeffel | |
| 2013/0069794 A1* | 3/2013 | Terwilliger | G06Q 10/08 |
| | | | 340/815.45 |
| 2014/0296755 A1 | 10/2014 | Lack et al. | |
| 2015/0216749 A1* | 8/2015 | Heil | A61G 7/0506 |
| | | | 5/613 |
| 2017/0061096 A1 | 3/2017 | Kelly et al. | |
| 2018/0181352 A1* | 6/2018 | Saito | G06F 3/1288 |
| 2020/0323354 A1* | 10/2020 | Newkirk | A61G 7/05769 |
| 2020/0381106 A1 | 12/2020 | Limaye et al. | |
| 2021/0350923 A1 | 11/2021 | McKirdy | |
| 2023/0195397 A1* | 6/2023 | Kado | G06K 19/06037 |
| | | | 715/705 |

* cited by examiner

SYSTEMS AND METHODS FOR RESOLVING AN ERROR CONDITION OF A MEDICAL DEVICE

PRIORITY CLAIM

This application claims priority under 35 U.S.C. § 119(e) to U.S. Provisional Application No. 63/381,669, filed on Oct. 31, 2023, which is expressly incorporated by reference herein.

BACKGROUND

The present disclosure relates to a system that permits to user to access information specific to an operating condition of a medical device from a location that is remote to the medical device. More specifically, the present disclosure relates to the automatic display of a code used by a user to access an interactive troubleshooting tool from a remote computer.

As patient support systems, such as hospital beds with therapy mattresses become more complex, the knowledge necessary to properly operate the functional systems expands. Furthermore, as the functionality of the patient support systems expands, the concern with interference by non-qualified individuals with the delivery of therapy by the patient support systems grows. A balance between the ease of use for a caregiver and the ability to address detailed errors is an important part of the development of user interfaces for patient support systems and patient support surfaces.

In the healthcare setting, caregivers come into contact with a wide variety of medical and patient care devices such as hospital beds, patient lifts, intravenous (IV) pumps, vital signs monitors, therapy delivery devices, and so forth. To control each of these patient care devices, caregivers must touch or otherwise contact user inputs such as buttons, knobs, and touch screens, of each individual patient care device. Caregivers also touch other types of equipment found in a patient room environment such as window blinds, thermostats, and light switches.

Each time a caregiver contacts a surface in a patient room, there is a risk that the caregiver becomes contaminated with germs or bacteria and there is a risk that the caregiver contaminates the surface with germs or bacteria. Accordingly, it would be beneficial to reduce the number of surfaces that a caregiver needs to contact in order to control multiple pieces of equipment in a patient room environment.

Currently, patient support systems use paper printed user manuals for hospital staff to reference. Because these can be difficult to find in hospitals, "Help" screens have been employed in patient support systems with graphical interfaces. This can be problematic because the Help screens often require a significant amount of memory.

SUMMARY

The present disclosure includes one or more of the features recited in the appended claims and/or the following features which, alone or in any combination, may comprise patentable subject matter.

According to a first aspect of the present disclosure, a system comprises a medical device, a mobile device, and a remote computer. The medical device includes a control system having a user interface having at least one display, and at least one controller. The controller includes a processor and a memory device, the memory device including instructions that, when executed by the processor, cause the controller to communicate an error condition to the user interface. The user interface includes a processor and a memory device, the memory device including instructions that, when executed by the processor, cause the user interface to display a machine readable indicia that is associated with a uniform resource locator (URL). The mobile device includes a camera, a processor, and a memory device that includes instructions that, when executed by the processor, cause the camera to detect a machine readable indicia and automatically connect to the internet and direct an internet browser of the mobile device to a URL associated with the machine readable indicia. The remote computer hosts an interactive menu driven webpage associated with the URL associated with the machine readable indicia. The mobile device is configured to display the menu driven webpage such that a user may interact with the menu driven webpage through the browser on the mobile device, the menu driven webpage operable to provide information specific to the error condition communicated to the user interface to allow the user to identify and resolve the error condition.

In some embodiments of the first aspect, the medical device is a patient support apparatus.

In some embodiments of the first aspect, the error condition is associated with a module of the medical device.

In some embodiments of the first aspect, the user interface of the medical device is operable to display a help key and, when the help key is activated during an error condition, the machine readable indicia generated by the user interface is associated with the specific error condition.

In some embodiments of the first aspect, prior to activation of the help key, a text box identifying the error condition is displayed on the user interface.

In some embodiments of the first aspect, the machine readable indicia includes a quick response (QR) code.

In some embodiments of the first aspect, the machine readable indicia includes a bar code.

In some embodiments of the first aspect, the machine readable indicia includes text that is both machine readable and man readable.

According to a second aspect of the present disclosure, a system comprises a medical device and a remote computer. The medical device includes a control system having a user interface having at least one display, and at least one controller. The controller includes a processor and a memory device, the memory device including instructions that, when executed by the processor, cause the controller to communicate an error condition to the user interface. The user interface includes a processor and a memory device, the memory device including instructions that, when executed by the processor, cause the user interface to display a machine readable code indicia that is associated with a uniform resource locator (URL). The remote computer hosts an interactive menu driven webpage associated with the URL associated with the machine readable indicia. When the URL is accessed by an internet browser, the internet browser displays the menu driven webpage such that a user to interact with the menu driven webpage through the browser, the menu driven webpage operable to provide information specific to the error condition communicated to the user interface to allow the user to identify and resolve the error condition.

In some embodiments of the second aspect, the medical device is a patient support apparatus.

In some embodiments of the second aspect, the error condition is associated with a module of the medical device.

In some embodiments of the second aspect, the user interface of the medical device is operable to display a help key and, when the help key is activated during an error condition, the machine readable indicia generated by the user interface is associated with the specific error condition.

In some embodiments of the second aspect, prior to activation of the help key, a text box identifying the error condition is displayed on the user interface.

In some embodiments of the second aspect, the machine readable indicia includes a quick response (QR) code.

In some embodiments of the second aspect, the machine readable indicia includes a bar code.

In some embodiments of the second aspect, the machine readable indicia includes text that is both machine readable and man readable.

According to a third aspect of the present disclosure, a method of resolving an error condition of a medical device comprises generating a man readable indication of the error condition on a display of the medical device. The method also comprises, in response to an input from a user activating a help function while the error condition is displayed, generating a machine readable indicia on the display of the medical device, the machine readable indicia corresponding to a uniform resource locator (URL) associated with the specific error condition. The method further comprises utilizing an optical detector to read the machine readable indicia, the optical detector configured to cause an internet browser to be opened and directed to the URL. The method still further comprises displaying, on the internet browser, a menu driven webpage associated with the URL. The method also yet further comprises providing, through the menu driven webpage, information specific to the error condition.

In some embodiments of the third aspect, the machine readable indicia comprises a quick response (QR) code.

In some embodiments of the third aspect, the machine readable indicia includes text that is both machine readable and man readable.

In some embodiments of the third aspect, the error condition is associated with a module of the medical device.

In some embodiments of the third aspect, if no error condition is present, activation of the help function results in a machine readable indicia that directs to a URL associated with a menu driven screen providing general user information for the medical device.

In some embodiments of the third aspect, the optical detector comprises a smart phone.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
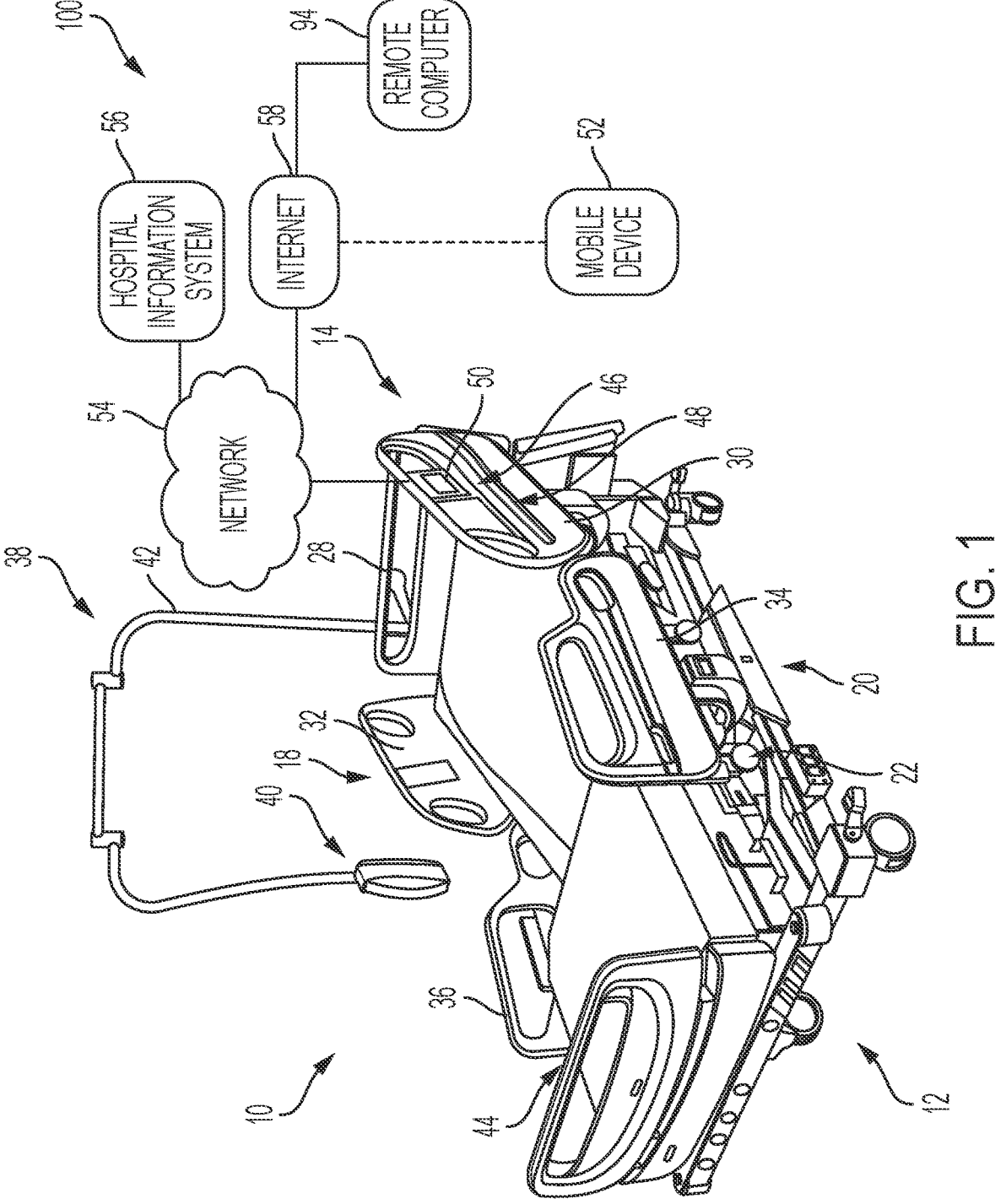
FIG. 1 is a diagrammatic view of a system that includes a patient support apparatus, a mobile computing device, and a network connected to a hospital information system and the internet.

Referring to FIG. 1, a medical device is disclosed as a patient support apparatus 10 is illustratively embodied as a hospital bed 10. In other embodiments, the medical device may be embodied as medical and patient care devices such patient lifts, intravenous (IV) pumps, vital signs monitors, therapy delivery devices, and the like. The hospital bed 10 includes an overhead arm assembly 38 that is used to provide support for a patient interface device 40. The view shown in FIG. 1 is generally taken from a position that is oriented at the left side, foot end of the hospital bed 10. For purposes of orientation, the discussion of the hospital bed 10 will be based on the orientation of a patient supported on the hospital bed 10 in a supine position. Thus, the foot end 12 of the hospital bed 10 refers to the end nearest the patient's feet when the patient is supported on the hospital bed 10 in the supine position. The hospital bed 10 has a head end 14 opposite the foot end 12. A left side 16 refers to the patient's left when the patient is lying in the hospital bed 10 in a supine position. The right side 18 refers to the patient's right. When reference is made to the longitudinal length of the hospital bed 10, it refers a direction that is represented by the lines that generally extend between the head end 14 and foot end 12 of the hospital bed 10. Similarly, lateral width of the hospital bed 10 refers to a direction that is represented by the lines that generally extend between the left side 16 and right side 18.

The hospital bed 10 includes a base frame 20 which supports a lift system 22. The lift system 22 engages the base and an upper frame 24 such that the lift system 22 moves the upper frame 24 vertically relative to the base frame 20. The lift system 22 includes head end and foot end linkages (not shown) that are independently operable and may be operated to cause the hospital bed 10 to move into a tilt position which is when the head end 14 of the upper frame 24 is positioned lower than the foot end 12 of the upper frame 24. The hospital bed 10 may also be moved to a reverse tilt position with the foot end 12 of the upper frame 24 is positioned lower than the head end 14 of the upper frame 24. The upper frame 24 supports a load frame and pivotable deck sections as known in the art.

A foot panel 26 (sometimes referred to as a footboard) is supported from the deck and extends vertically at the foot end 12 of the hospital bed 10. A head panel 28 (sometimes referred to as a headboard) is positioned the base frame 20 and extends vertically to form a barrier at the head end 14 of the hospital bed 10. A left head siderail 30 is supported from the deck and is moveable between a raised position shown in FIG. 1 and a lowered position as is known in the art. A right head siderail 32 is also moveable between the raised position of FIG. 1 and a lowered position. The left head siderail 30 illustratively includes a user interface 46 that includes a keypad 48 and a touchscreen interface 50.

The hospital bed 10 also includes a left foot siderail 34 and a right foot siderail 36, each of which is supported by the upper frame 24. Each of the siderails 30, 32, 34, and 36 are operable to be lowered to a position below an upper surface of the respective deck section. It should be noted that when the head portion of the deck is moved, the head siderails 30 and 32 move with the deck so that they maintain their relative position to the patient. The overhead arm assembly 38 is supported from the upright structure 42. A mattress 44 is supported on the deck and movable with the deck as is known in the art.

The hospital bed 10 is a portion of an information management system 100 that includes an optical reader device shown as a mobile device 52 which is embodied as a smart phone. However, the mobile device may be embodied as a tablet computer, a personal digital assistant, a smart phone, or a laptop computer. The information management system 100 also includes a network 54 which is connected to the hospital bed 10 as well as a hospital information system 56 and the internet 58. The mobile device 52 may communicate with the internet through any of a number of known ways. For example, access to the internet may be achieved by use of any one or more communication technologies (e.g., wired or wireless communications) and associated protocols (e.g., Ethernet, InfiniBand®, Bluetooth®, Wi-Fi®, WiMAX, 3G, 4G LTE, 5G, etc.) to effect such communication. A remote computer 94 is also connected to the internet 58 and may use any of the above noted communication technologies or other suitable communication technology. The remote computer 94 hosts uniform resource locator (URL) pages according to the present disclosure and is accessible to other components of the system 100 through the internet 58. In some embodiments, the remote computer 94 may be directly accessible to other components of the system 100 through the network 54.

Figure 2:
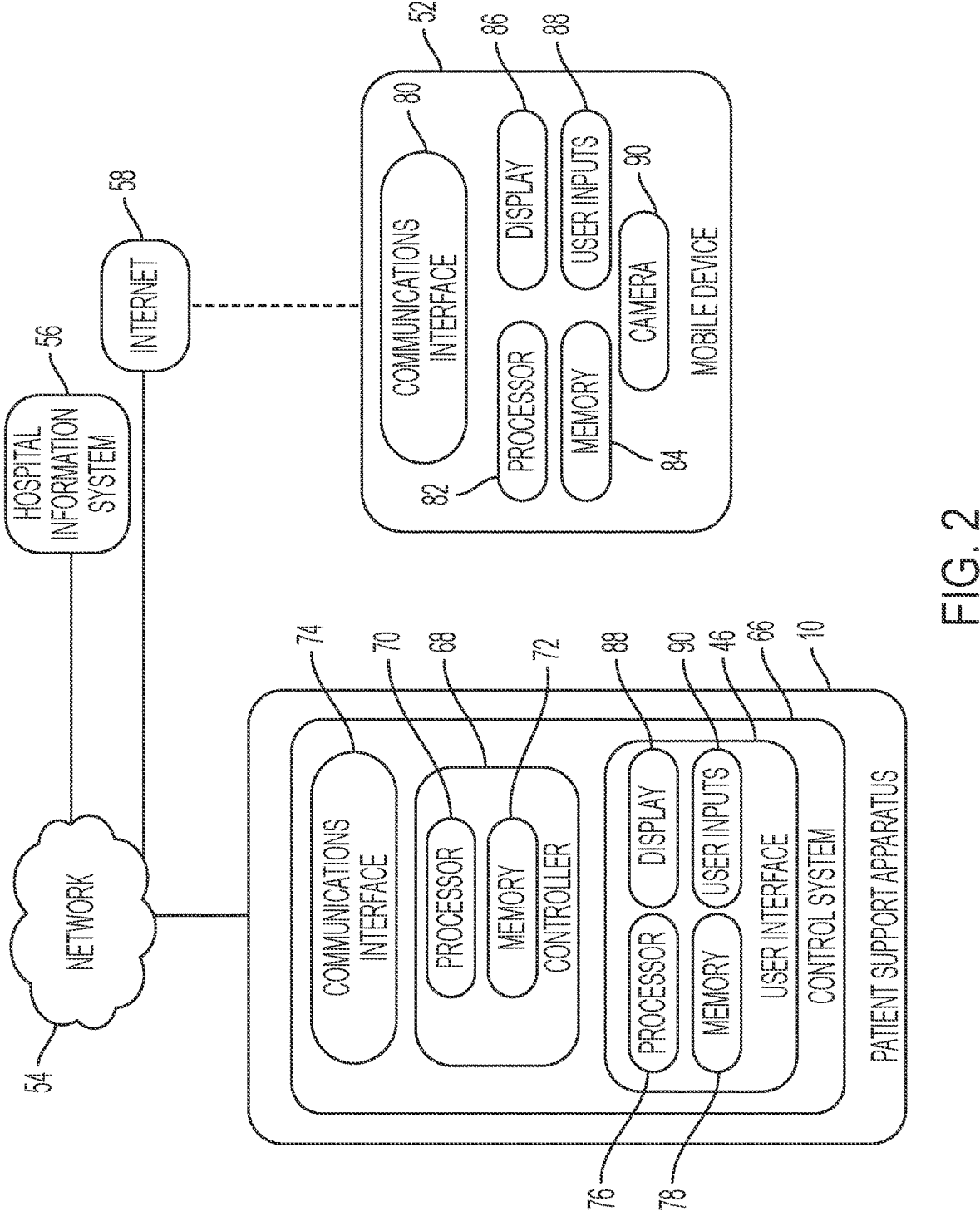
FIG. 2 is a block diagram of the aspects of the system of FIG. 1 described in this disclosure.

A control system 66 for the hospital bed 10 is shown in FIG. 2 and includes a controller 68 which includes a processor 70 and a memory device 72. Operation of the hospital bed 10 is controlled by the processor 70 which executes instructions stored in the memory device 72 to effect operation of the hospital bed 10 according to the present disclosure. It should be understood that the control system 66 may include multiple controllers with specific functionality distributed to separate controllers having specific functions for functional subsystems or modules of the patient support apparatus 10. The multiple controllers may each communicate with one another via a network, with one or more of the controllers in communication with the network 54.

The control system 66 further includes communications interface 74 that is operable to communicate with the network 54. The control system 66 further includes the user interface 46 that includes a display 86 and a plurality of user inputs 88. In some the illustrative embodiment the user interface 46 includes the display 50 which illustratively is a touchscreen display which allows a user to provide inputs through the display 50. The user interface 46 also includes the keypad 48 which is shown in FIG. 2 as user inputs 48. The user interface includes a processor 76 and a memory device 78. Operation of the user interface 46 is controlled by the processor 76 which executes instructions stored in the memory device 78 to effect operation of the user interface 46. The processor 76 of the user interface 46 may interact with the processor 70 of the controller 68 using any of a number of communications protocols known in the art, including, but not limited to, Echelon, CAN, SPI, and LIN or another suitable electronic communications protocol. In still other embodiments, the communications may include circuitry that allows for a hardwired connection using an IEEE 802.3 connection, an RS-232 compliant connection, an RS-483 compliant connection, or other protocols known in the art.

The mobile device 52 includes a communications interface 80 and a processor 82 and a memory device 84. Operation of the mobile device 52 is controlled by the processor 82 which executes instructions stored in the memory device 84 to effect operation of the mobile device 52. The mobile device 52 further includes a display 86 which illustratively is a touchscreen display which allows a user to provide inputs through the display 50. The mobile device 52 also includes discrete user inputs 88, and a camera 90. In some embodiments, the user inputs 88 may be omitted and the user may use only the touchscreen functionality of the display 86. It should be understood that in some embodiments, the communications interface 80 is operable to communicate via a wireless protocol that include Bluetooth®, IEEE 802.11n (Wi-Fi), IEEE 802.16e (WiMAX), mobile communications technologies such as 3G or 4G technology, or other wireless technology. In still other embodiments, the communications interface 80 may include circuitry that allows the mobile device 52 to communicate via a hardwired connection using an IEEE 802.3 connection, an RS-232 compliant connection, an RS-483 compliant connection, or other protocols known in the art.

The control system 66 of the hospital bed 10 may include a number of functional subsystems or modules as is known in the art. These subsystems may be complex subsystems that involve the sharing of data between subsystems to control various functional aspects of the hospital bed 10. These subsystems/modules may encounter conditions in which the operation of the hospital bed 10 or resolution of error conditions within the hospital bed 10 may not be readily apparent to a user. The present disclosure is directed to a system which provides a user ready access to operational information and troubleshooting functions in real-time, while limiting the amount of information that must be stored on the hospital bed 10.

Figure 5:
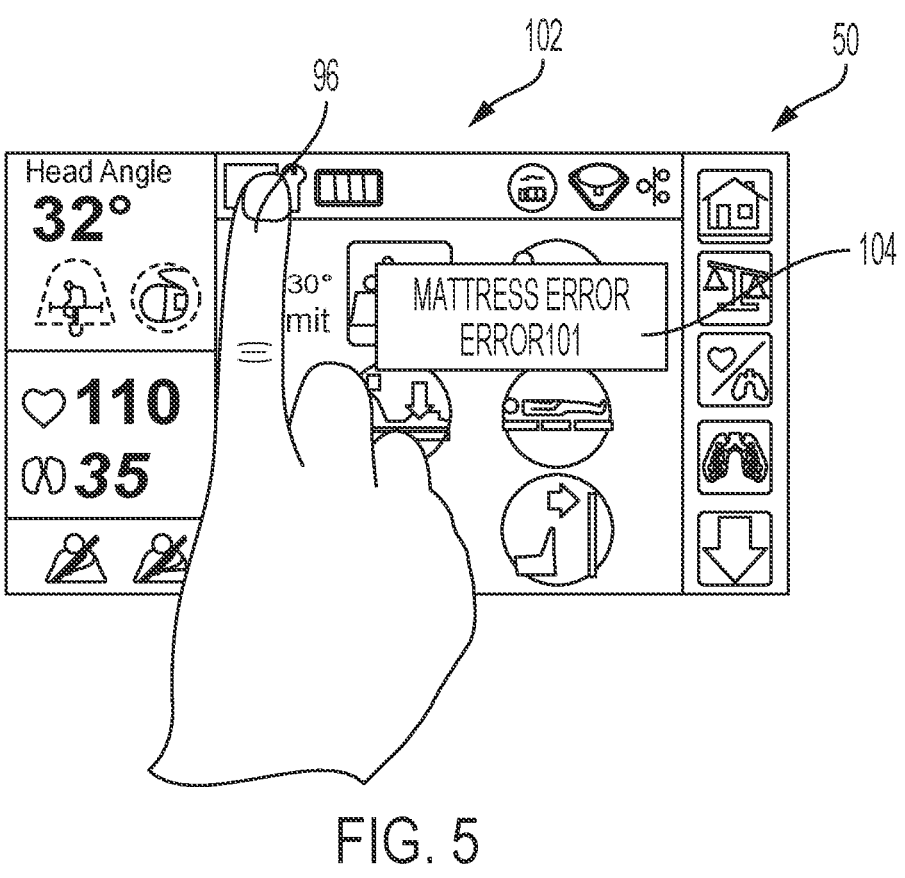
FIG. 5 is an illustration of a help key being actuated on the display according to the present disclosure.

The touchscreen 50 provides the user with an interactive screen that may be used to access useful information for the user regarding the operation of the hospital bed 10 or any errors being experienced by the hospital bed 10. For example, referring to FIG. 5, a screen 102 displayed on the touchscreen 50 displays an error notification 104 indicating that the module for the mattress 44 is in an error condition. A user may activate a help key or icon 106 (seen in FIG. 6) with their finger 96 to activate a help screen 108 (shown in FIG. 6) which provides a machine readable indicia, such a QR code 110, that the user may scan with the mobile device 52 to access reference materials from a URL on the internet associated with the particular QR code 110. In some embodiments, the user interface 40 may include a touchscreen similar to touchscreen 50 and the functionality associated with touchscreen 50 could be available on user interface 40 when it is so equipped.

Figure 9:
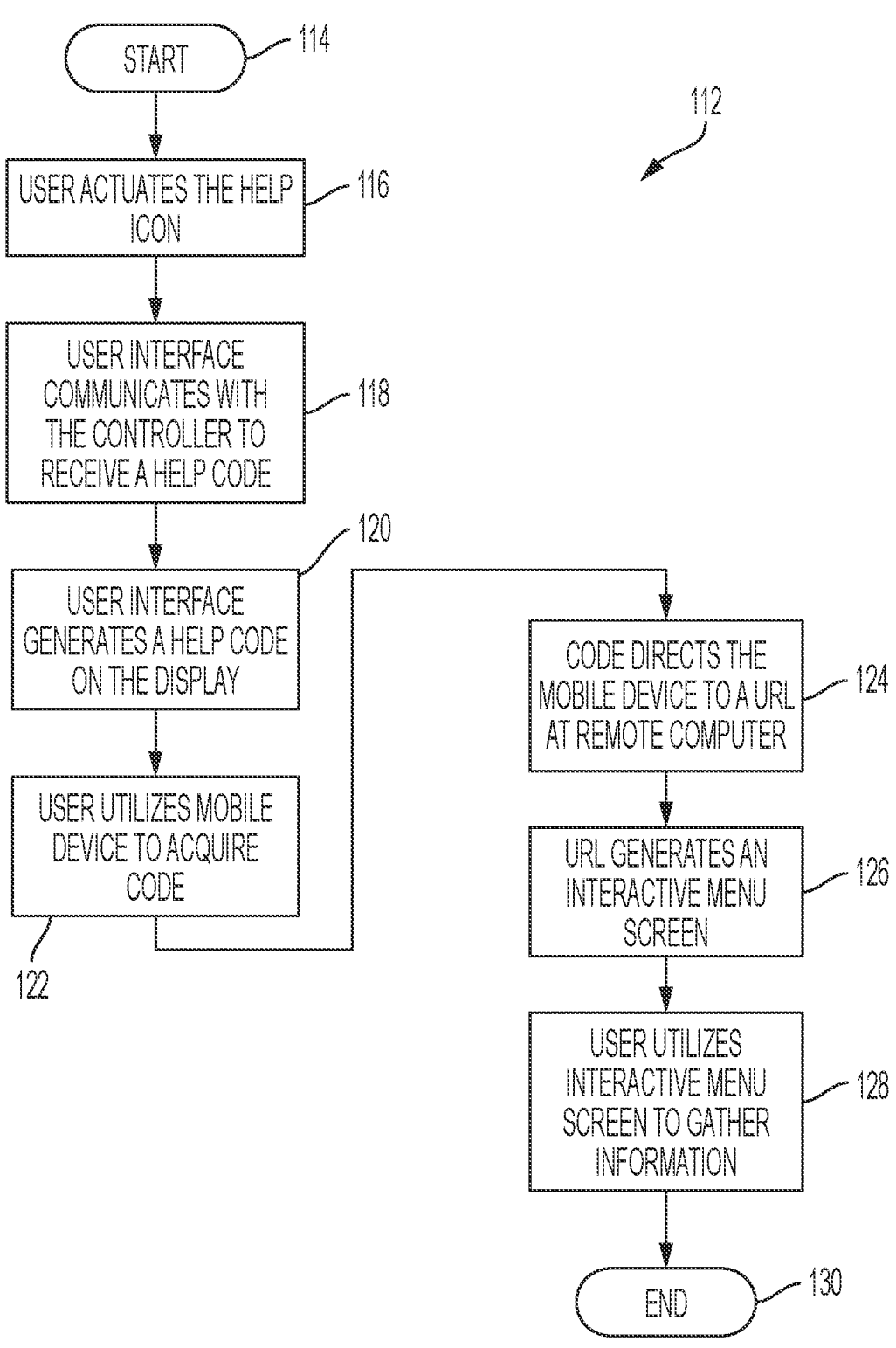
FIG. 9 is a flowchart showing the flow of steps of the present disclosure when a user is searching for reference information.

Referring now to FIG. 9, a general process 112 for utilizing this approach is shown. The user starts the process at step 114 and actuates the help key 106 at step 116. The user interface 46 communicates this state to the controller 68 at step 118 where the controller 68 provides a value that represents the help request and the controller 68 forwards value to the user interface 46. At step 120 the processor 76 of the user interface 46 processes the value and generates the QR code 110 specific to that value and displays the QR code 110 on the screen 108.

The QR code 110 is available to the user who may use the camera 90 of the mobile device 52 to allow the mobile device 52 to read the QR code 110 as indicated at step 122. The processor 82 of the mobile device 52 processes the QR code 110 and communicated to the internet 58 through a link 92 (shown in FIG. 1) to direct an internet browser application on the mobile device 52 to access a URL associated with the QR code 110 as indicated at step 124.

Figures 7, 8:
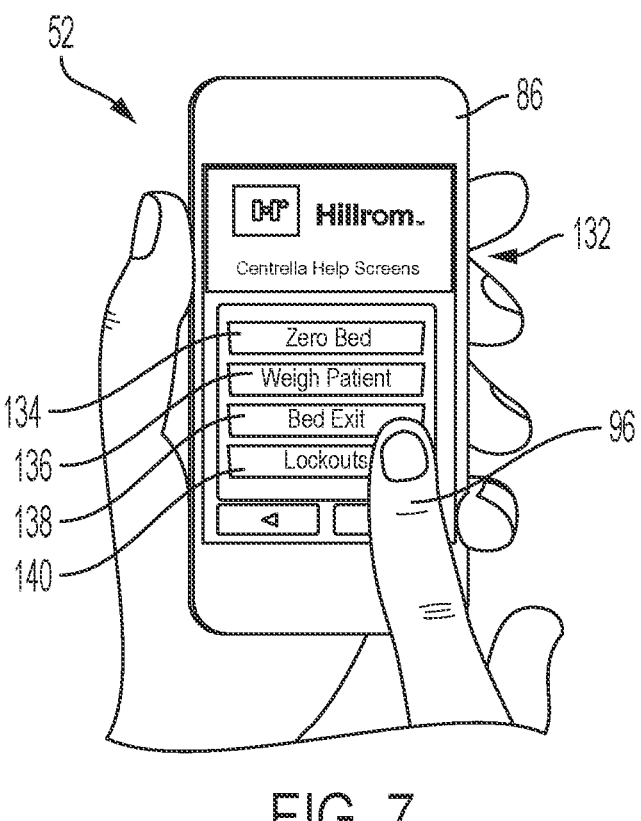
FIG. 7 is an illustration of a menu displayed on a mobile device that is generated when one of the displays shown in FIGS. 4-6 is entered into the mobile device.
FIG. 8 is an illustration of the information displayed on the mobile device upon activation of the button being activated in FIG. 7.

At step 126 the URL generates an interactive menu screen, such as a menu screen 132 shown on the display 86 of the mobile device 52 in FIG. 7, used by the user to navigate through various subjects that may be of interest to the user, based on the activation of the help key 106. In should be understood that in some embodiments, the screen 132 may be a display screen only and the help key 106 may be a discrete key present on the keypad 48. The menu screen 132 of FIG. 8 displays a number of selectable radio buttons 134, 136, 138, and 140 that correspond to functions of the hospital bed 10 including "Zero Bed", "Weigh Patient", "Bed Exit", and "Lockouts." At step 128, the user utilizes the interactive menu screen 132 to gather information. For example, using their finger 96 to interact with the menu screen 132 to activate the "Lockouts" radio button as illustrated in FIG. 7, the menu advances to a screen 142 shown in FIG. 8 which provides a quick reference for a user to explain how the "Lockouts" function of the hospital bed 10 works. It should be understood that the interactive menu at the URL could have any of a number of various branches and options to allow a user to navigate through information that is helpful for operating the hospital bed 10 or provides information useful to the user. Once the user has completed their interaction, process 112 ends at step 130.

Figure 10:
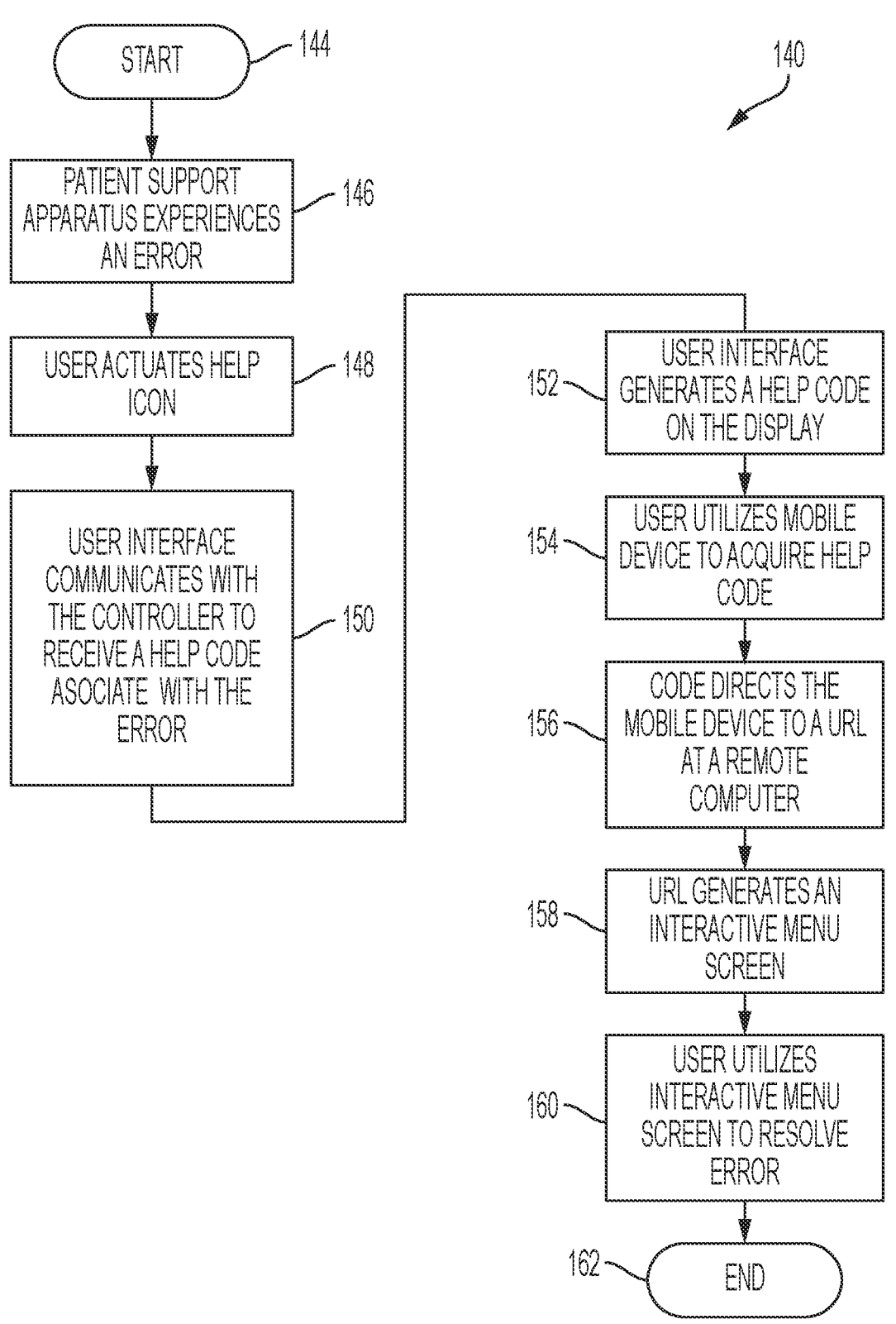
FIG. 10 is a flowchart showing the flow of steps of the present disclosure when a user is addressing an error condition on the patient support apparatus.

In addition to the embodiment of FIG. 9, in some embodiments, the QR code 110 may be tailored to a particular error condition and another process 140 shown in FIG. 10 may be utilized by a user to address the specific error code. For example, the mattress error code is given as ERROR101 in FIG. 5. Referring to process 140, the process starts at step 144 and then advances to step 146 where the error code is generated. At step 148, the user actuates the help key 106, similarly to the discussion above. The user interface 46 communicates the activation of the help key 106 to the controller 68 at step 150. However, because the ERROR101 is active at the time, the controller 68 generates a help code associated with the particular error and transmits the value associated with that help code to the user interface 46. At step 152 the user interface 46 generates a QR code 110 that is associated with a specific URL for the particular error code, ERROR101 in this example.

The user utilizes the mobile device 52 to read the QR code 110 at step 154 and the internet browser of the mobile device 52 is directed to the URL specific to the error code at step 156. This, in turn, generates an interactive menu screen specific to the error code at step 158. The user then utilizes the interactive menu at step 160 to resolve the error condition. Once the error condition is resolved, the process ends at step 162.

Figure 3:
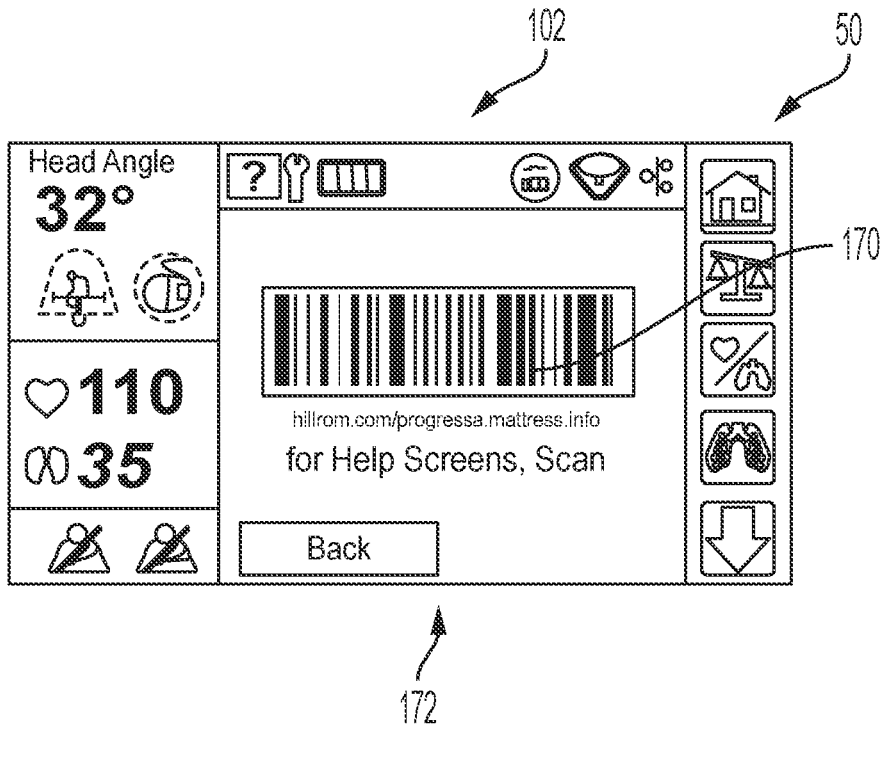
FIG. 3 is an illustration of a user screen on a display of the patient support apparatus of FIGS. 1 and 2.
Figure 4:
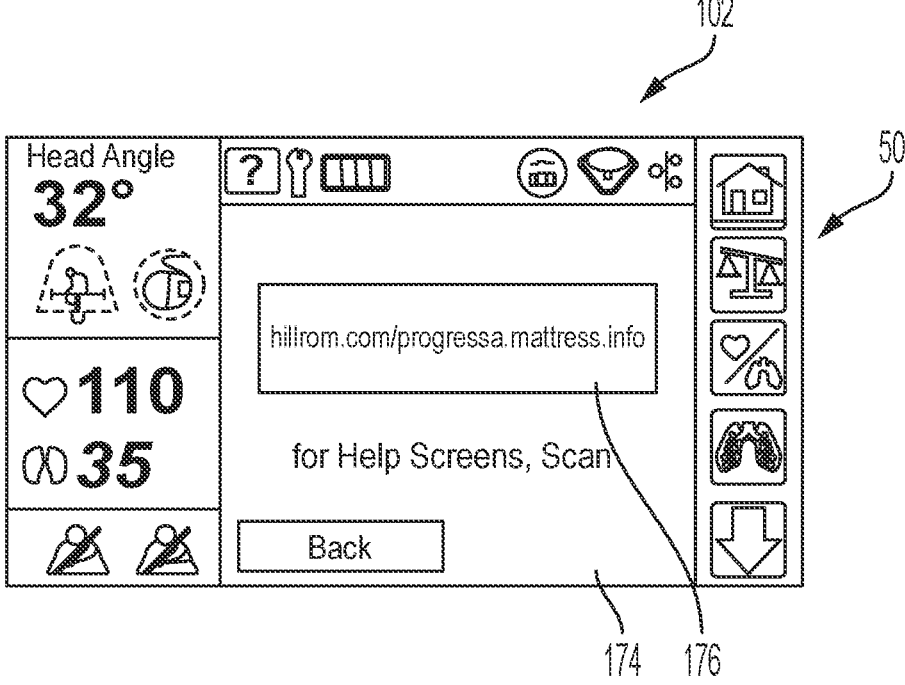
FIG. 4 is an illustration of one embodiment of a screen that may be displayed in response to the actuation of the help key.
Figure 6:
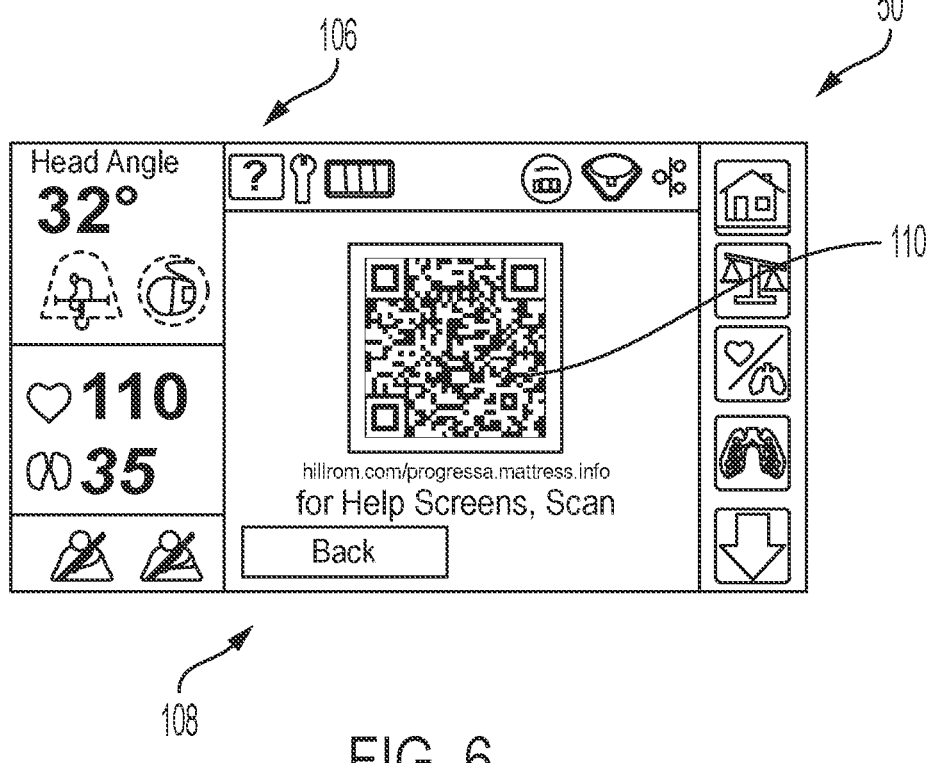
FIG. 6 is an illustration of a second embodiment of a screen that may be displayed in response to the actuation of the help key.

It should be understood that in addition to QR code 110 embodiment of FIG. 4, other machine and or man readable indicia may be generated. In the embodiment FIG. 3, a bar code 170 is displayed on a screen 172, the bar code 170 providing machine readable indicia which functions similarly to the QR code 110. Similarly, in the embodiment FIG. 4, a text code 176 is generated on a screen 174. The text code 176 in the embodiment of FIG. 6 is both machine and man readable. While the text code 176 is operable to direct an internet browser to the corresponding URL, the text of the text code 176 corresponds to the appropriate URL such that, if a machine reader is not available, a user can type the appropriate URL address into the internet browser.

Although this disclosure refers to specific embodiments, it will be understood by those skilled in the art that various changes in form and detail may be made without departing from the subject matter set forth in the accompanying claims. The disclosure is not limited to the disclosed embodiments. From reading the present disclosure, other modifications will be apparent to a person skilled in the art. Such modifications may involve other features, which are already known in the art and may be used instead of or in addition to features already described herein. In the claims, the word "comprising" does not exclude other elements or steps, and the indefinite article "a" or "an" does not exclude a plurality.

The invention claimed is:

1. A system comprising:
   a medical device including a control system having (i) a user interface having at least one display and (ii) at least one controller associated with a first functional subsystem, the controller including a first processor and a first memory device, the first memory device including instructions that, when executed by the first processor, cause the at least one controller to communicate a signal indicating a first error condition for the first functional subsystem to the user interface, the user interface including a second processor and a second memory device, the second memory device including instructions that, when executed by the second processor, cause the user interface to receive the signal indicating the first error condition from the at least one controller associated with a first functional subsystem and in response to the signal indicating the first error condition, generate and display machine readable indicia that is associated with a uniform resource locator (URL) related to the first error condition of the first functional subsystem; and
   a remote computer hosting an interactive menu driven webpage associated with the URL associated with the machine readable indicia;
   wherein, when the URL is directly accessed by an internet browser when a mobile computing device scans the machine readable indicia, the internet browser displays the menu driven webpage such that a user can interact with the menu driven webpage through the browser, the menu driven webpage operable to provide information specific to the first error condition communicated to the user interface to allow the user to identify and resolve the first error condition.

2. The system of claim 1, wherein the medical device is a patient support apparatus.

3. The system of claim 1, wherein the user interface is operable to receive a second error condition associated with a second functional subsystem of the medical device.

4. The system of claim 1, wherein the user interface of the medical device is operable to display a help key and, when the help key is activated during the first error condition, the machine readable indicia generated by the user interface is associated with the first error condition.

5. The system of claim 4, wherein prior to activation of the help key, a text box identifying the first error condition is displayed on the user interface.

6. The system of claim 4, wherein the medical device is a patient support apparatus.

7. The system of claim 4, wherein the user interface is operable to receive a second error condition is associated with a second functional subsystem of the medical device.

8. The system of claim 4, wherein the machine readable indicia includes a quick response (QR) code.

9. The system of claim 4, wherein the machine readable indicia includes a bar code.

10. The system of claim 4, wherein the machine readable indicia includes text that is both machine readable and man readable.

11. A method of resolving an error condition of a medical device comprising:

receiving a signal indicating a first error condition of a first functional subsystem by a user interface of the medical device;

generating a man readable indication of the first error condition in response to the signal on a display of the user interface of the medical device;

in response to an input from a user activating a help function while the first error condition is displayed, the user interface generating a machine readable code indicia and displaying on the display of the user interface of the medical device, the machine readable indicia corresponding to a uniform resource locator (URL) associated with the first error condition of the first functional subsystem;

utilizing an optical detector to read the machine readable indicia, the optical detector configured to cause an internet browser to be opened and directed to the URL when the machine readable indicia is scanned;

displaying, through the internet browser, a menu driven webpage associated with the URL; and providing, through the menu driven webpage, information specific to the first error condition.

12. The method of claim 11, wherein the machine readable indicia comprises a quick response (QR) code.

13. The method of claim 11, wherein the machine readable indicia includes text that is both machine readable and man readable.

14. The method of claim 11, wherein the user interface is operable to receive a second error condition is associated with a second functional subsystem of the medical device.

15. The method of claim 14, wherein if no error condition is present, activation of the help function results in a machine readable indicia that directs to a URL associated with a menu driven screen providing general user information for the medical device.

16. The method of claim 11, wherein if no error condition is present, activation of the help function results in a machine readable indicia that directs to a URL associated with a menu driven screen providing general user information for the medical device.

17. The method of claim 16, wherein the machine readable indicia comprises a quick response (QR) code.

18. The method of claim 16, wherein the machine readable indicia includes text that is both machine readable and man readable.

19. The method of claim 16, wherein the user interface is operable to receive a second error condition that is associated with a second functional subsystem of the medical device.

20. The method of claim 16, wherein the optical detector comprises a smart phone.

\* \* \* \* \*